Figure 1:
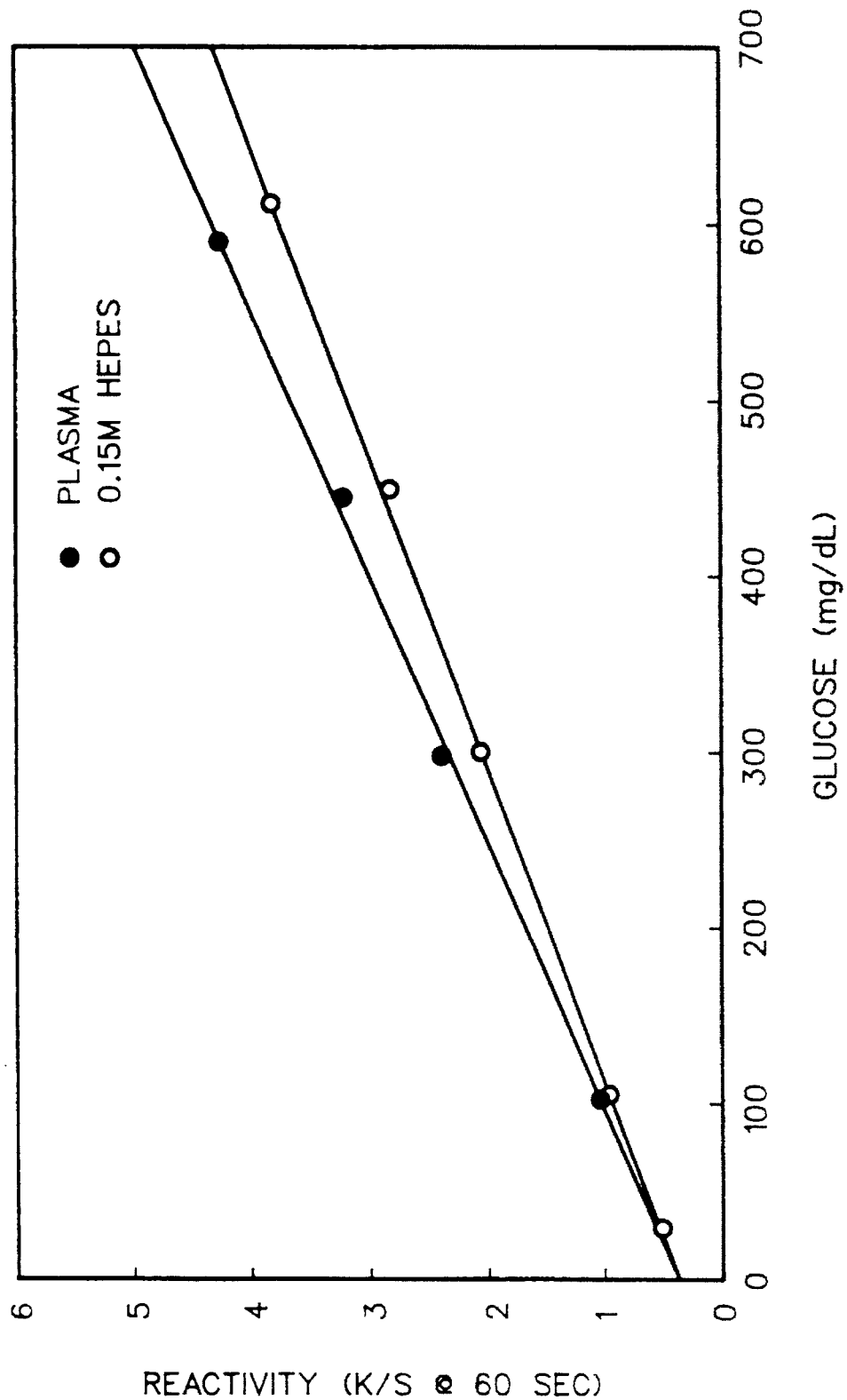

United States Patent

Bell et al.

Patent Number: 5,453,378
Date of Patent: Sep. 26, 1995

[54] DIAGNOSTIC TEST SYSTEM VERIFICATION METHOD USING SERUM FREE GLUCOSE CONTROL CONTAINING QUATERNARY AMMNONIUM POLYMER

[75] Inventors: Douglas E. Bell; Amy H. Chu, both of Elkhart; Karen L. Marfurt, Mishawaka, all of Ind.

[73] Assignee: Miles Inc., Elkhart, Ind.

[21] Appl. No.: 201,372

[22] Filed: Feb. 24, 1994

[51] Int. Cl.$^6$ ................................. G01N 31/00
[52] U.S. Cl. .................. 436/14; 436/8; 436/12; 436/13; 436/15; 436/16
[58] Field of Search ..................... 436/8, 12–16, 436/19

[56] References Cited

U.S. PATENT DOCUMENTS

| | | | |
|---|---|---|---|
| 3,920,580 | 11/1975 | Mast | 436/15 X |
| 4,141,856 | 2/1979 | Dorwart, Jr. et al. | 436/19 X |
| 4,536,186 | 8/1985 | Rey | 44/51 |
| 4,668,508 | 5/1987 | Grollier et al. | 424/70 |
| 4,753,888 | 6/1988 | Chiang | 436/19 X |
| 5,028,542 | 7/1991 | Kennamer et al. | 436/14 |

FOREIGN PATENT DOCUMENTS

| | | | |
|---|---|---|---|
| 266216 | 5/1988 | European Pat. Off. | 436/16 |
| 62-194461 | 8/1987 | Japan | 436/16 |
| 3-255021 | 11/1991 | Japan . | |
| 4-99709 | 3/1992 | Japan . | |

OTHER PUBLICATIONS

K. Pommerenin et al. World patents Abstracts 83–747635/35.
Yu. A. Klyacho et al. *Vinodel. Vinograd. SSSR* 1984, 51–53.
V. A. Izumrudov et al, *Dokl. Akad. Nauk SSSR* 1986, 291, 1150–1154.
S. R. Marouchoc *Cosmetics & Toiletries* 1977, 92, 91–93.
K. Stanzl et al. *Chem. Abstr.* 1982, 97, 222 732g.
E. Kokufuta et al. *Macromolecules* 1982, 15, 1618–1621.
D. Horn et al, *J. Bio. Chem.* 1983, 258, 1665–1670.
M. Rosen et al. *J. Soc. Cosmet. Chem.*, 1984, 35, 157–169.
Y. A. Klyachko et al. Chem. Abstr. 1985, 102, 60703r.
V. A. Izumrudov et al. Chem. Abstr. 1987, 107, 92146f.
J. M. Park et al. *Macromolecules* 1992, 25, 290–295.

*Primary Examiner*—James C. Housel
*Assistant Examiner*—Arlen Soderquist
*Attorney, Agent, or Firm*—Jerome L. Jeffers

[57] ABSTRACT

Disclosed is a serum free control reagent formulation useful for the determination of a pre-selected analyte. The formulation involves an aqueous solution of a predetermined amount of the analyte together with a polymerized quaternary salt of di- or mono- allyl, di- or tri- alkyl ammonium characterized by the formulae:

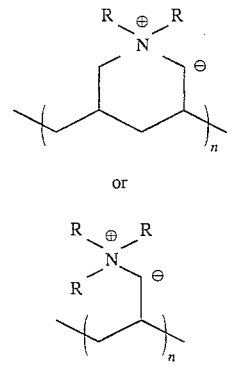

where R is straight or branched chain alkyl of 1 to 4 carbon atoms, n is a number of at least 9 and θ represents a counteranion. The formulation typically contains a buffer to maintain its pH at a level of about 7.5 and a preservative.

9 Claims, 2 Drawing Sheets

DIAGNOSTIC TEST SYSTEM VERIFICATION METHOD USING SERUM FREE GLUCOSE CONTROL CONTAINING QUATERNARY AMMNONIUM POLYMER

VERIFICATION METHOD USING SERUM FREE GLUCOSE CONTROL CONTAINING QUATERNARY AMMONIUM POLYMER

BACKGROUND OF THE INVENTION

The field of clinical chemistry is concerned with the detection and quantification of various substances in body fluids. Included among those substances which can be determined are cholesterol and glucose, urea, as well as cations such as calcium and potassium which are found in various body fluids such as urine and blood.

One of the most frequently used analytical devices in clinical chemistry is the test strip which is contacted with the body fluid to be tested. Various reagents incorporated into the test strip react with the analyte to be determined in the body fluid to provide a detectable signal which is typically a change in color. These color changes are measured either visually or, where greater accuracy is required, spectrophotometrically. The detected signal is correlated to a standard to thereby give a value for the amount of analyte in the sample.

Clinical analysis of the type described above, especially when automated systems are used, must necessarily be extremely accurate to ensure that the measurement taken is valid. Control reagents are used to verify this accuracy by determining that the device is giving the correct response.

A control reagent is a specimen or solution which is analyzed solely for quality control purposes and is not used for calibration. A suitable control reagent should be stable and available in aliquots or vials so that it can be analyzed periodically over a long time. There should be little or no aliquot-to-aliquot or vial-to-vial variation so that differences between repeated measurements can be attributed to the analytical method alone.

Modified human serum known in the art as "control serum" is one type of control material. One of the requisites of a control material is stability. Control materials based upon serum, however, are inherently unstable due to the various components contained therein. In addition, sera will vary from source to source thereby rendering unpredictable the reproducibility of the results of using control serum from different lots. Control reagents, with which the present invention is concerned, are control materials which are not based on, and do not contain, serum of any type.

U.S. Pat. No. 3,920,580 discloses that control reagents for glucose determinations can be prepared without any serum or components thereof by incorporating an antidiffusing agent into a glucose/water solution. The antidiffusing agents disclosed in this patent include polyvinylpyrrolidone, polyvinyl alcohol, polyethylene glycol, dextran and bovine serum albumin.

U.S. Pat. No. 5,028,542 discloses a glucose control reagent comprising a predetermined amount of glucose, water and polystyrenesulfonate or a soluble salt thereof.

These prior art control reagents are somewhat limited in that their stability, compatibility with the tetrazolium salt indicators used in certain test strips, and surface tension are all lower than that of serum. We have discovered a particular class of polymers for use in these control reagents which enhance the solubility of tetrazolium salt indicators and thereby improve the performance of the control reagent.

SUMMARY OF THE INVENTION

The present invention is a serum free control reagent for the determination of a pre-selected analyte which comprises an aqueous solution of the analyte together with a polymerized quaternary salt of di- or mono- allyl, di- or tri- alkyl ammonium characterized by the formulae:

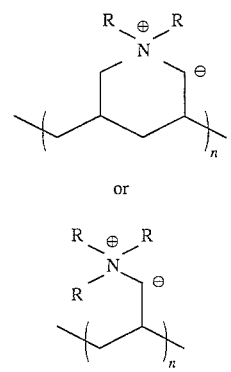

or copolymers thereof. In the foregoing formulae, R is straight or branched chain alkyl of 1 to 4 carbon atoms, n is a number of at least 9 representing the degree of polymerization and $\theta$ represents a counteranion.

Optionally, the formulation also contains a buffer, a colorant and a preservative.

DESCRIPTION OF THE INVENTION

The basic formulation of the cationic quaternary ammonium polymer and water is used as a base to which analytes such as glucose, BUN, sodium, protein and uric acid are added to prepare aqueous controls for diagnostic test systems.

The formulation is suitable for the control of the accuracy and precision of methods of determination using automatic analyzers by using a control reagent containing the analyte to be determined in a known and precisely fixed concentration.

Many aqueous controls contain polymers such as polyvinylpylpyrrolidone, and polyvinylalcohol in their formulation. The present invention involves the use of a synthetic, water soluble polymer of the type previously described in a stabilized buffer system for use in aqueous diagnostic controls. This control system is especially useful in conjunction with dry reagent strip assays in which a redox indicator, particularly a tetrazolium salt, and a reagent system, which upon rehydration will elicit a detectable response in the indicator upon exposure to a pre-selected analyte, are uniformly dispersed in a matrix material. The cationic polymer is useful as a thickening agent to reduce the migration of reagents in the reaction layer (via chromatography) to provide more uniform color in the reacted reagent pad and control assay kinetics by the rate of reaction (diffusion) since the rate of wetting affects the final result. The surface active properties of the polymerized quaternary ammonium compounds of the present invention e.g. poly(diallylmethyl ammonium)chloride (PDDA) and its analogs are distinguished from PVP and PVA in that the polymers of the present invention help with the wetting of dry reagent pads thereby limiting the need for the addition of other surfactants to the formulation. While polystyrene sulphonate is known to possess surface active properties, it differs from the polymers used in the present system in that it is negatively charged while PDDA and its analogs are positively charged.

In preparing the present reagent system, the polymer is dissolved in water (preferably distilled) up to a level to provide a solution with the desired viscosity and wetting properties. Typically, this will involve a concentration of from 0.5 to 5.0 weight % (preferably 0.2 to 2.0%) depending on the particular polymerized quaternary ammonium compound selected and the polymer's molecular weight. These polymers are prepared by polymerizing allyl or diallyl quaternary ammonium salts in which the valence bonds of the nitrogen not occupied by an allyl group are occupied by straight or branched chain alkyl groups of 1–4 carbon atoms. These salts and the polymers obtained by their polymerization typically have a halide, e.g. chloride or bromide, as the counteranion but may be combined with other counteranions such as acetate or sulfonate. Poly(diallyldimethyl ammonium) chloride, PDDA, is the polymer of choice for use in the present invention and can be obtained from Polysciences, Inc. The degree of polymerization of these polymers, i.e. the value of n in the above formula, is typically from about 800 to 2300 with a degree of polymerization of from about 1100 to 1900 being preferred.

The other essential ingredient is, of course, the analyte of interest. The following discussion is directed to glucose as the analyte of interest with the understanding that it is equally applicable to other analytes.

The glucose used is typically D-glucose of a high grade so that an accurate quantity will be included in the control solution. D-glucose and dextrose are regarded as equivalent materials for use in this invention and may be substituted one for the other. Although the amount of glucose in the solution is not critical within its solubility limits, the control solution will typically contain from about 1–1,000 mg% (mg/100 ml solution). Within this range, control reagents can be prepared containing glucose within the normal range (80 to 120 mg/dL) and the pathological range (250 to 500 mg/dL).

It is beneficial to include a preservative in the control reagent to prevent microbial growth therein. Suitable preservatives include benzoic acid, sodium benzoate, dichlorophene, hexachlorophene, sorbic acid, phosphoric acid and esters of p-hydroxybenzoic acid. A preferred preservative is Dowicil 200preservative, whose active ingredient is [cis-1-(3-chloroallyl)-3,5,7-triaza-1-azoniadamantane chloride] (95%) and which contains hexamethylenetetramine hydrochloride (5%) (w/v) as residual starting material, due to its ability to maintain antimicrobial activity at a neutral pH as opposed to benzoate which is not an effective preservative at pH 7.5. Typical concentrations of the preservative in the formulation are from 0.1 to 0.5% by weight.

The control reagent is preferably buffered to a pH of about 7.5 since this is close to the physiological pH of blood. Since the type of reagent pad under consideration is designed for use with blood, the control solution should mimic blood as closely as possible with respect to physical properties, one of which is pH. Suitable buffers include HEPPS (N-2-hydroxyethylpiperazine-N'-3-propanesulfonic acid); MOPS [3-(N-Morpholino)propanesulfonic acid] and HEPES [4-(2-hydroxyethyl)-1-piperazine ethane sulfonic acid]. HEPES is particularly suitable due to its ability to buffer solutions to pH 7.5.

Further adjuvants may be added to the control solution to impact a particular color or physical appearance. A red blood color which is desirable in this sort of formulation to assist the user in applying the control solution to the correct area of the reagent strip may be obtained by incorporating a red, water insoluble laine dye into the formulation. Red dye #40 works well for this purpose. This is significant because it is difficult to see whether the drop is correctly applied to the application site when the solution is colorless.

The present invention is further illustrated by the following example.

EXAMPLE

Aqueous glucose control reagents were formulated as follows:

37.4 g/L (1.5 M) HEPES 0.5 sodium salt 0.4 g/L FD&C Red Dye #40

Glucose at 30, 100, 300, 450 and 600 mg/dL.

One reagent contained 60 g/L of poly(diallyldimethyl ammonium)chloride and the other contained no polymer. Each of the control reagent was tested on a technique independent dry reagent glucose format using human plasma as a control with the reactivity (in terms of K/S values) being determined at 60 seconds after application of the control reagent and the plasma containing the indicated glucose concentrations.

Figure 2:
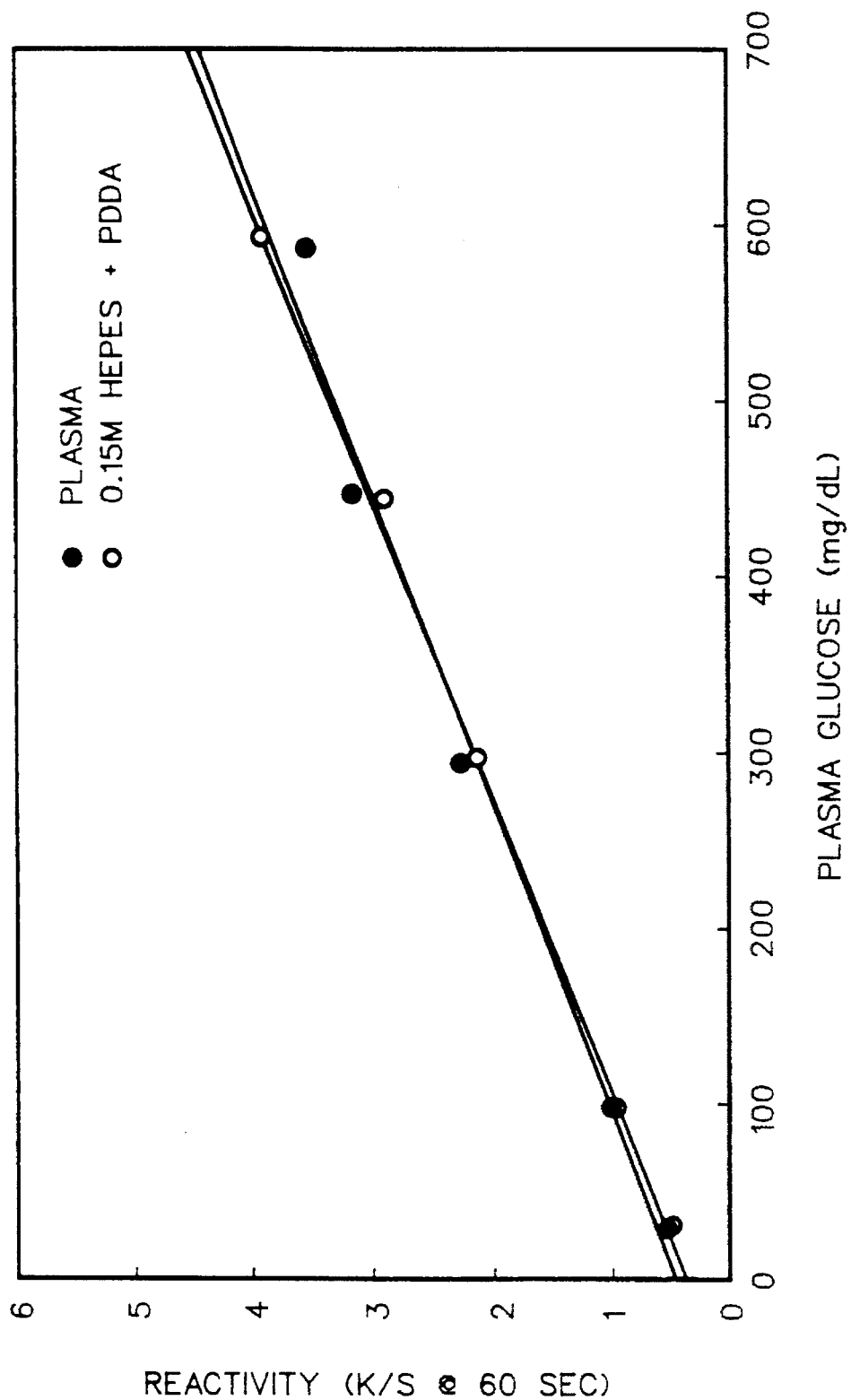

The results of this experiment using the polymer free control reagent are set out in FIG. 1 with the results obtained using the PDDA containing control reagent being graphically illustrated in FIG. 2. These figures demonstrate that the reactivity of the control reagent containing the polymer of the present invention is much closer to that of plasma than is that of the control reagent without the polymer.

What is claimed is:

1. In a method for verifying the accuracy of an automated system for use in clinical analysis of glucose comprising reacting a glucose determining reagent with a control reagent containing a known amount of glucose, measuring a response for the reaction, and determining if the system is giving the correct response, the improvement which comprises using a serum free control reagent formulation for determination of the glucose which reagent comprises an aqueous solution of a predetermined amount of the glucose together with a preservative and a polymerized quaternary salt of di- or mono- allyl, di- or trialkyl ammonium having the formulae:

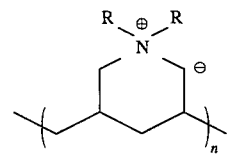

or

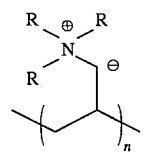

or copolymers thereof wherein R is straight or branched chain alkyl of 1 to 4 carbon atoms, n is a number of at least 9 and θ represents a counteranion and wherein said formulation contains a buffer capable of buffering it to a pH of about 7.5.

2. The method of claim 1 wherein the quaternary salt is a salt of the poly(diallylmethyl ammonium) cation.

3. The method of claim 2 wherein the anion is chloride, bromide, acetate or sulfonate.

4. The method of claim 3 wherein the anion is chloride.

5. The method of claim 1 wherein the polymerized quaternary salt is present in a concentration of from 0.5 to 5.0 weight percent of the control formulation.

6. The method of claim 1 wherein the polymerized quaternary salt is present in a concentration of from 0.2 to 2.0 weight percent.

7. The method of claim 1 wherein glucose is present in either the normal range of 80 to 120 mg/dL or the pathological range of 250 to 500 mg/dL.

8. The method of claim 1 wherein the preservative is cis-1-(3-chloroalloy)-3,5,7-triaza-1-azonia-damantane chloride.

9. The method of claim 1 wherein the buffer is 4-(2-hydroxyethyl)-1-piperazine ethane sulfonic acid.

* * * * *